United States Patent [19]

Katz et al.

[11] Patent Number: 5,764,068
[45] Date of Patent: Jun. 9, 1998

[54] METHOD FOR MEASURING MECHANICAL PROPERTIES OF THIN FILMS USING A RESONATOR IN AN ANTI-RESONANCE REGIME

[75] Inventors: Alexander Katz, Pasadena, Calif.; Michael D. Ward, Minnetonka, Minn.

[73] Assignee: California Institute of Technology, Pasadena, Calif.

[21] Appl. No.: 686,006

[22] Filed: Jul. 25, 1996

Related U.S. Application Data

[60] Provisional application No. 60/001,433 Jul. 25, 1995.
[51] Int. Cl.$^6$ .......................... G01N 3/32; G01N 27/02; G01R 29/22
[52] U.S. Cl. .......................... 324/727; 324/652; 324/71.1; 73/778
[58] Field of Search ..................... 324/601, 633, 324/652, 727, 109, 71.1; 73/579, 763, 778

[56] References Cited

U.S. PATENT DOCUMENTS

| | | | |
|---|---|---|---|
| 4,621,233 | 11/1986 | Davari et al. | 324/727 |
| 4,703,216 | 10/1987 | Corbett | 73/778 X |
| 5,201,215 | 4/1993 | Granstaff et al. | 73/54.41 |
| 5,211,054 | 5/1993 | Muramatsu et al. | 73/64.42 |

OTHER PUBLICATIONS

Mason, et al., "Measurement of Shear Elasticity and Viscosity of Liquids at Ultrasonic Frequencies", *Physical Review*, vol. 75, No. 6, Mar. 15, 1949, pp. 936–946.

Barlow, et al., "The Visco–Elastic Behavior of Lubricating Oils Under Cyclic Shearing Stress", *Proc. R. Soc. A*, vol. 253, 1959, pp. 52–68 (month unavailable).

K. H. Berhndt, "Long–Term Operation of Crystal Oscillators in Thin–Film Deposition", *J. Vac. Sci. Technol*, vol. 8, No. 5, 1971, pp. 622–626 (month unavailable).

K. K. Kanazawa, "Using The Quartz Resonator With Polymer Films", ANTEC '90, 1990, pp. 1049–1053 (month unavailable).

Reed, et al., "Physical Description of a Viscoelastically Loaded AT–Cut Quartz Resonator", *J. Appl. Phys.*, vol. 68, Sep. 1990, pp. 1993–2001.

Martin, et al., "Polymer Film Characterization Using Quartz Resonators", Ultrasonics Symposium Proceedings, 1991, pp. 393–398 (month unavailable).

J. W. Grate, et al., "Acoustic Wave Microsensors", *Anal. Chem.*, vol. 65, No. 22, Nov. 15, 1993, pp. 987–996.

A. Katz, "A Quartz Resonator–Based Rheometer For The Dynamic Investigation Of Viscoelastic Films", Thesis, University of Minnesota, Aug. 1994, pp. 1–148.

Katz, et al., "Probing Solvent Dynamics In Concentrated Polymer Films With a High–Frequency Shear Mode Quartz Resonator", *J. Appl. Phys*, vol. 80, No. 7, Oct. 1996, pp. 4135–4163.

*Primary Examiner*—Glenn W. Brown
*Attorney, Agent, or Firm*—Fish & Richardson P.C.

[57] ABSTRACT

A method using quartz resonators probes dynamically the mechanical characteristics of thin films. This method probes the film properties at the anti-resonance frequency where the vibrational amplitude is smallest, minimizing nonlinear contributions in the dependence of the film mechanical characteristics on the resonator electrical characteristics. Determination of the mechanical characteristics involves impedance analysis, transformation of |Y| and θ data into a linear form so that the conductance and susceptance at the frequency of minimum absolute admittance can be accurately determined, and use of a two-dimensional Newton-Raphson numerical method to determine the values of the storage modulus G', loss modulus G", as well as various other film and resonator properties.

16 Claims, 7 Drawing Sheets

５，７６４，０６８

METHOD FOR MEASURING MECHANICAL PROPERTIES OF THIN FILMS USING A RESONATOR IN AN ANTI-RESONANCE REGIME

STATEMENT AS TO FEDERALLY SPONSORED RESEARCH

The U.S. Government has certain rights in this invention pursuant to Grant No. CTS-9111000 awarded by the National Science Foundation.

CROSS REFERENCE TO RELATED APPLICATIONS

This utility application is a conversion of copending U.S. Provisional application Ser. No. 60/001,433, filed Jul. 25, 1995 by Alexander Katz and Michael Ward.

FIELD OF THE INVENTION

The invention relates to measuring mechanical properties of thin films, and more particularly to a method for measuring mechanical properties using a resonator that operates in an anti-resonance regime where the amplitude of mechanical displacement during resonator oscillation is minimized.

BACKGROUND AND SUMMARY

The study of properties of materials forms much of the basis of applied sciences. Mechanical properties are one class of material properties that is often of interest.

Thin films are conveniently employed when studying mechanical properties of materials. Thin film properties, mechanical and otherwise, may often be more simply modeled and measured than their bulk counterparts. Thin films also have significant technological applications in diverse areas such as paints, laminates, adhesives, and advanced coating technologies. The mechanical properties of these films determines to a large extent their feasibility for a particular application. Thin film properties measured often relate to viscoelastic characteristics concerning the films' resistance to movement when subjected to a stress.

Viscoelastic properties of thin films have been studied by placing a thin film in contact with a quartz resonator. A resonator is a piezoelectric crystal that resonates, i.e., produces mechanical displacements of significant amplitude among the atoms of the crystal when an alternating voltage with a specific frequency is applied between certain faces of the crystal. Commonly, resonators made of quartz are used because of their exceptional mechanical stability, high quality factor, relatively high electromechanical coupling factor, and availability of cuts that can translate in a precise mode of motion.

A quartz resonator in intimate contact with a thin film forms the basis for a composite resonator comprising the quartz and thin film layers. The piezoelectric oscillations of the quartz induce movement in the atoms or molecules of the thin film, causing the mechancial and electrical characertistics of the quartz resonator to change from its unloaded value. Various studies have measured mechanical properties of thin films by measuring these changes. For example, frequency changes have been related to the mass of the thin film contacting the quartz resonator. In this way, the quartz resonator can be used to measure the mass of the thin film. This value may in turn be related to thickness and so on. Other studies have related mechanical properties to the resonant frequency and resonant resistance of the quartz resonator.

The prior art has most often measured quartz resonator electrical characteristics at the resonance frequency corresponding to or in the regime of maximum absolute admittance, i.e., the frequency at which the atoms of the quartz resonator oscillate with maximum amplitude. The present inventors went against this established teaching by measuring quartz resonator electrical characteristics in an anti-resonance condition, corresponding to minimum vibrational amplitude, rather than the common resonance condition in the regime of maximum vibrational amplitude. Indeed the difference between these two regimes can be significant, as some studies have shown that the absolute admittance at the maximum vibrational amplitude can be greater than at the minimum by at least five orders of magnitude. The present inventors further yet developed a method and means to measure mechanical properties of thin films given the anti-resonant electrical characteristics of a quartz resonator in a composite resonator configuration. Thin film storage and loss moduli are among the properties that may be accurately measured once the anti-resonant electrical characteristics are known. Hence, the invention provides a method for determining mechanical properties of thin films which are difficult or impossible to obtain by other experimental methods.

Properties of quartz resonators can also be determined by this method. Storage and loss moduli are among the properties that may be measured. Hence, the invention provides a method for determining mechanical properties of thin films which are difficult or impossible to obtain by other methods.

In one embodiment, the method uses a quartz resonator in contact with a thin film. The quartz resonator is commanded to oscillate in an anti-resonance condition, i.e., in a small frequency range near the minimum magnitude of the complex electrical admittance of the oscillator. In this small frequency range, the quartz resonator's amplitude of vibration is substantially minimized. This small frequency range may be initially chosen by a process of estimation or by conducting an initial scan over a larger frequency range.

Once the small frequency range is determined, the quartz resonator is commanded to oscillate at a number of frequencies within the small range. An impedance analyzer measures the complex electrical admittance as a function of frequency. In particular, the impedance analyzer measures the magnitude and phase angle of the electrical admittance at each frequency within a given range. The actual values of the magnitude and phase angle are determined at the point of minimum absolute admittance or, equivalently, minimum magnitude of the complex admittance.

The amplitude of vibration of the quartz crystal atoms is substantially minimized at the point of minimum absolute admittance. This minimum amplitude allows a linear electromechanical model to be used which relates the magnitude and phase angle, determined by the above step, to various mechanical properties such as storage modulus, loss modulus, and glass transition properties.

In another embodiment, properties of a quartz resonator not in contact with a thin film are measured. A quartz resonator is again caused to oscillate in a small frequency range near that of the minimum electrical admittance of the oscillator where the amplitude of vibration is substantially minimized. An impedance analyzer is used to measure the complex admittance of the bare quartz crystal over a period of time.

The stability over time of the crystal's admittance can be a significant indicator of its quality. By measuring the stability over time using the method above, an accurate prediction may be made as to the quality of the quartz resonator. Quartz resonators may also be calibrated using the method.

An advantage of the method is that a large amount of information is provided about the crystal/film or bare crystal system under investigation, since three independent antiresonant electrical characteristics are measured simultaneously, as opposed to a frequency measurement alone, for example, which only measures one.

DETAILED DESCRIPTION OF THE PREFERRED EMBODIMENT

Figure 1:
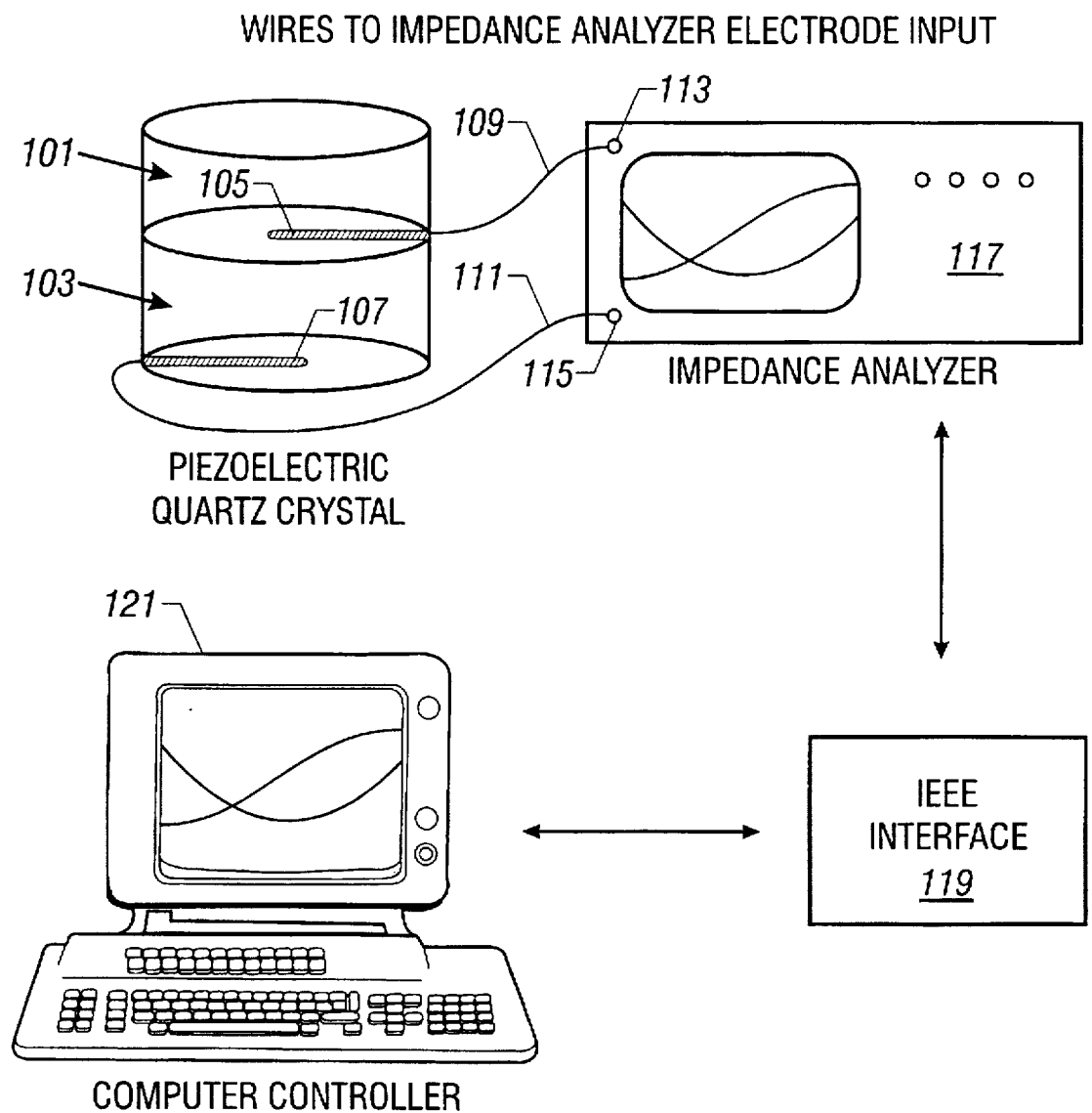
FIG. 1 is a diagram of an experimental setup implementing an embodiment of the invention.

FIG. 1 shows a block diagram of an experimental setup implementing an embodiment of the invention including a film 101 coating a crystal 103. Crystal 103 is usually piezoelectric; a voltage applied across electrodes 105 and 107 causes a vibration of the crystal atoms. A 5.0 MHz biconvex crystal having a diameter of 0.34 inches can be used for this purpose.

An impedance analyzer 117 applies a voltage to crystal 103. Piezoelectric crystal 103 vibrates in response to the voltage. The mechanical vibration may be characterized by a complex admittance and characteristic frequency. Impedance analyzer 117 receives admittance data from crystal 103 by leads 109 and 111 which are connected to contacts 105 and 107, respectively. These leads and contacts may both apply voltage and be used for measuring admittance. In other systems, a separate set of leads and contacts may be used to perform one of these functions.

An impedance analyzer which may be used is a Hewlett-Packard HP 4194A equipped with an HP 16047D test fixture in the |Y|–θ mode with an output voltage of 1 volt. Here |Y| represents the absolute value of the admittance and θ represents the phase angle. The number of averaging points may be about eight (i.e., a data point is measured eight times) and the integration time 2 (this value is specific to the HP 4194A, and corresponds to a medium amount of dwell time for each data point).

Impedance analyzer 117 measures the absolute admittance and phase angle of the vibrations of crystal 103 as a function of frequency and relays these values to a computer controller 121 through an IEEE interface 119. IEEE interface may be an IOtech IEEE 488 interface. Computer 121 runs a control program to determine the values of the desired mechanical properties. Computer 121 may be, for example, a Macintosh SE/30 personal computer.

Figure 2:
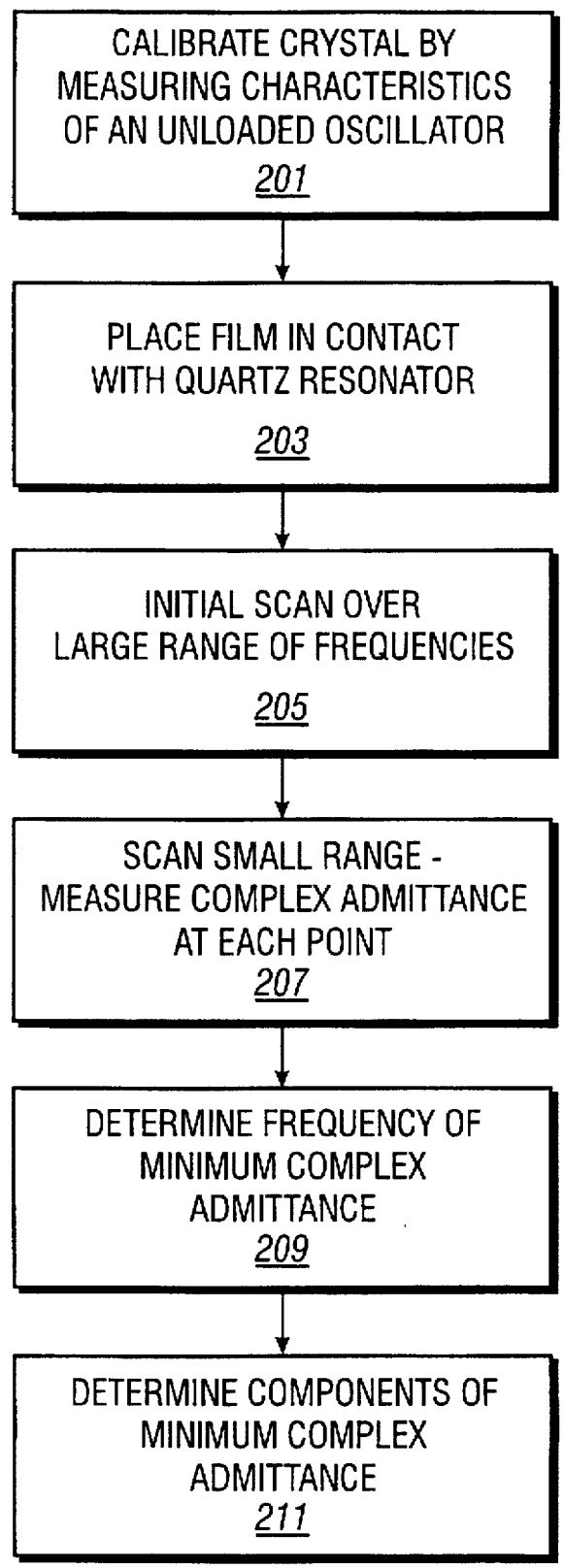
FIG. 2 is a flowchart of a method of an embodiment of the invention.

FIG. 2 is a flowchart of an embodiment of a method according to the invention, beginning with the calibration of a bare crystal 103 (step 201), also referred to as an unloaded oscillator. The calibration determines the piezoelectric active area $A_{ACT}$, the resonant frequency $f_r$, and the quartz viscosity $\eta_q$. The crystal calibration is described in more detail below. After calibration, film 101 to be studied is placed in contact with crystal 103 (step 203). For example, film 101 may be coated on crystal 103.

Impedance analyzer 117 performs an initial scan over frequency f to determine anti-resonance frequencies, i.e., minimum frequencies in the magnitude of the complex admittance |Y|–θ (step 205). This scan may be performed over a relatively wide range of frequencies. From this large scan a smaller range is chosen which surrounds a single minimum $f_{Ymin}$. This smaller range is chosen by examining at what frequencies the magnitude of the complex admittance has a minimum and also at what frequencies the shear vibrational amplitude is a minimum. In particular, the smaller range is chosen as the range surrounding the global minimum of the magnitude of the complex admittance for a resonating condition, i.e., the point of anti-resonance. The magnitude has additional local minima at various "overtones", however none of these represent the global minimum.

The motion of crystal 103 and film 101 can be described by linear equations of motion with significant accuracy at these small amplitudes. Use of these linear equations of motion allows approximations to the mechanical properties. These equations and approximations are described in detail below.

Impedance analyzer 117 then performs a more detailed scan over frequency f in the small range. The complex admittance Y is measured as a function of frequency at many points in this small range (step 207). Y may be separated into two parts: a real component $G_{fY}$ corresponding to conductance and an imaginary component $\beta_{fY}$ corresponding to susceptance. The same information may be represented by the magnitude |Y| and the phase angle θ of Y. |Y| and θ are measured by impedance analyzer 117 and may be later converted into $G_{fY}$ and $\beta_{fY}$.

Figure 3:
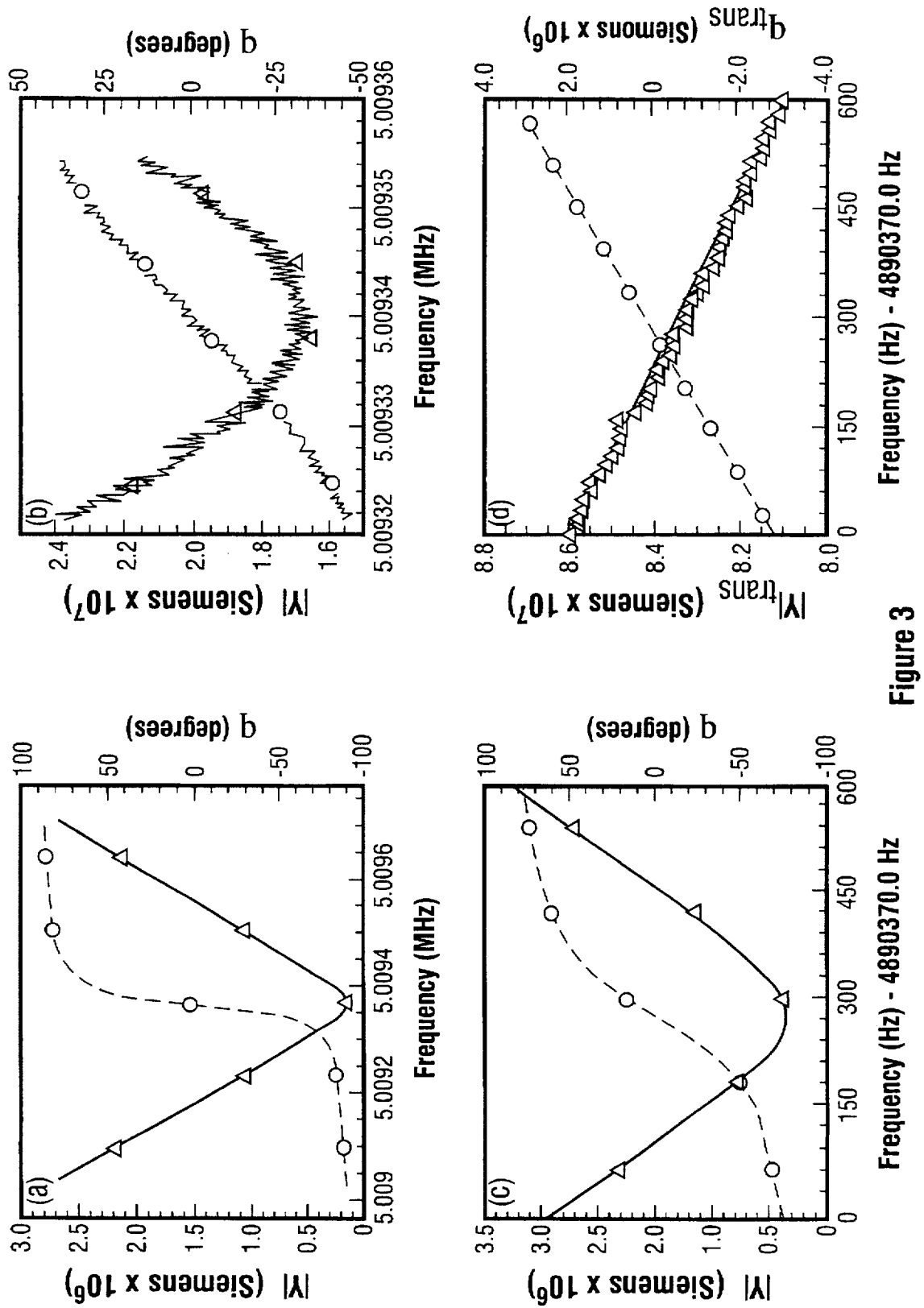
FIGS. 3(a)–(d) are graphs of the magnitude and phase angle of admittance versus frequency for an unloaded quartz crystal collected over (a) an 800 Hz span and (b) a 34 Hz span; also shown are graphs of (c) untransformed and (d) transformed magnitude and phase angle of admittance versus frequency for an unloaded quartz crystal collected over a 600 Hz span.

Accurate measurement of $G_{fYmin}$ and $\beta_{fYmin}$ relies on accurate determination of |Y| and θ at $f_{Ymin}$. However, locating $f_{Ymin}$ in admittance data is difficult because |Y| has a shallow minimum near $f_{Ymin}$. Signal noise also makes the determination difficult, the magnitude of which is often comparable to the changes in |Y| in this region. Furthermore, as shown in FIG. 3(a), θ (represented by the dashed curve) changes steeply and is nearly discontinuous about $f_{Ymin}$, passing through zero near $f_{Ymin}$. Even minute errors in the determination of $f_{Ymin}$ can result in large uncertainties in θ and in correspondingly large errors in the calculated values of $G_{fYmin}$ and $\beta_{fYmin}$.

FIG. 3(b) shows the effect of reducing the frequency span to limits required for accurate determination of $f_{Ymin}$. This figure reveals the difficulties posed by electric noise and the shallow minimum in |Y|. Direct determination of $f_{Ymin}$ from this data gives $f_{Ymin}$=5009338.68 Hz and $\theta_{fYmin}$=−1.9°. However, a negative resonant phase angle at $f_{Ymin}$ cannot occur in a simple quartz crystal and film system. Therefore, direct determination is unsatisfactory because the above-noted difficulties cause significant errors in |Y| and θ. Other curve fits of |Y| also fail to give physically consistent results.

The present invention also includes a novel procedure that may be used to overcome the above-mentioned difficulties in accurately measuring $G_{fYmin}$, $\beta_{fYmin}$, and $f_{Ymin}$. The procedure involves the transformation of the nonlinear dependence of |Y| and θ on frequency into two transformed variables that depend surprisingly linearly on frequency. These variables are defined by eqs. (1) and (2) below where $Y_{trans}$ represents the transformed admittance and $\theta_{trans}$ represents the transformed phase angle. Both $Y_{trans}$ and $\theta_{trans}$ are coupled functions of |Y| and θ and have units of admittance. These particular transformation functions are such that $Y_{trans}$ and $\theta_{trans}$ are equivalent to the conductance and the susceptance, respectively. However, this is purely coincidental, as any linear combination of eqs. (1) and (2) would define transformed variables that need not be equal to the conductance or susceptance but that nonetheless would be suitable.

$$Y_{trans} = \frac{|Y|}{\sqrt{1+\tan^2\theta}} = G \quad (1)$$

The utility of the transformation can be illustrated by considering the untransformed |Y|−θ data $$\theta_{trans} = \frac{|Y|\tan\theta}{\sqrt{1+\tan^2\theta}} = \beta \quad (2)$$

in the vicinity of $f_{Ymin}$ for a typical unloaded quartz resonator (see FIG. 3(c)). This data is transformed in FIG. 3(d) using eqs. (1) and (2), and results in linearized functions. The equations of these two lines can be described by eqs. (3) and (4) below.

$$Y_{trans} = Y_0 + m_1 f = G \quad (3)$$

$$\theta_{trans} = \theta_0 + m_2 f = \beta \quad (4)$$

The terms $Y_0$, $m_1$, $\eta_0$ and $m_2$ can be determined by a least squares regression. The frequency of minimum absolute admittance can be calculated (step 209 of FIG. 2) by expressing the absolute admittance as a function of the transformed variables:

$$|Y| = (Y_{trans}^2 + \theta_{trans}^2)^{1/2} \quad (5)$$

The above expression is differentiated with respect to frequency f, and the result is set equal to zero to obtain an expression for the frequency of minimum absolute admittance as a function of the regression coefficients. The result is given below:

$$f_{Ymin} = \frac{Y_0 m_1 + \theta_0 m_2}{m_1^2 + m_2^2} \quad (6)$$

where $f_{Ymin}$ represents the frequency of minimum absolute admittance.

The values of $G_{fYmin}$ and $\beta_{fYmin}$ can then be determined (step 211 of FIG. 2) by evaluating eqs. (3) and (4) at $f=f_{Ymin}$.

The measured values of $G_{fY}$ and $\beta_{fY}$ are used to obtain the desired values of mechanical properties by comparing these measured values with calculated theoretical values obtained from the linear electromechanical model. The theoretical values are calculated using estimates of the mechanical properties. Once the theoretical values converge to the measured values, the correct estimates of mechanical properties have been found. This technique is described below.

The theoretical values of $G_{fY}$ and $\beta_{fY}$ are determined by equation (7), disclosed by Reed et al. in the *Journal of Applied Physics*, vol. 68, 1993 (1990), which relates $$Y = \frac{\frac{i\omega A_{ACT}e_{22}}{l_q}[k_q \overline{\overline{c_{66}}}\sin(k_q l_q) + k_F \overline{\overline{\mu_F}}\tan(k_F l_F)\cos(k_q l_q)]}{k_q\overline{\overline{c_{66}}}\sin(k_q l_q) + k_F\overline{\overline{\mu_F}}\tan(k_F l_F)\cos(k_q l_q) - \frac{2e_{26}^2}{l_q \epsilon_{22}}\left[1 - \cos(k_q l_q) + \frac{k_F\overline{\overline{\mu_F}}}{2k_q\overline{\overline{c_{66}}}}\tan(k_F l_F)\sin(k_q l_q)\right]} \quad (7)$$

the complex admittance Y to various film properties. In Eq. (7), $$k_q = \omega\sqrt{\frac{\rho_q}{\overline{\overline{c_{66}}}}}$$

and $$k_F = \omega\sqrt{\frac{\rho_F}{\overline{\overline{\mu_F}}}}$$

$$\overline{\overline{c_{66}}} = c_{66} + \frac{e_{26}^2}{\epsilon_{22}} + i\omega\eta_q$$

and $\mu_F$ is the film shear modulus (or equivalently, the storage modulus G'), $\eta_F$ is the film viscosity (or equivalently, the loss modulus-frequency quotient G''/ω), $$\overline{\overline{\mu_F}} = \mu_F + i\omega\eta_F$$

$\rho_F$ is the film density, $l_F$ is the film thickness, $\rho_q$ is the quartz density, ω is the angular frequency (ω=2πf), $l_q$ is the quartz thickness, $\xi_{22}$ is the quartz dielectric constant, $e_{26}$ is the quartz piezoelectric constant, $c_{66}$ is the quartz shear modulus, and as before $\eta_q$ is the quartz viscosity and $A_{ACT}$ is the piezoelectric active area.

This equation is derived from linear equations of motion relating the electrical admittance to the mechanical properties of a composite resonator. These linear equations of motion, Eq. (8) and (9), are equations for shear motion in the quartz layer:

$$T_{12} = c_{66}\frac{\partial u_1}{\partial y} + \eta_q\frac{\partial}{\partial t}\frac{\partial u_1}{\partial y} + e_{26}\frac{\partial u_1}{\partial y} \quad (8)$$

where $T_{12}$ is the pertinent component of the stress tensor, $u_1$ represents the strain, $\eta_q$ is the viscosity of quartz, $$D_{12} = e_{26}\frac{\partial u_1}{\partial y} - \epsilon_{22}\frac{\partial \phi}{\partial y} \quad (9)$$

$c_{66}$ is the elastic shear modulus of quartz, $\epsilon_{22}$ is the quartz dielectric constant, $D_2$ is the electric displacement vector in the quartz, and $\phi$ is the electric potential constant for quartz, which represents the electromechanical coupling between the electric potential $\phi$ and the strain u.

The corresponding equation in the film is:

$$T_{12} = \mu_L\frac{\partial u_1}{\partial y} + \eta_L\frac{\partial}{\partial t}\frac{\partial u_1}{\partial y} \quad (10)$$

where $\mu_L$ is the elastic shear modulus of the film and $\eta_L$ is the viscosity of the film.

Y can be separated into real and imaginary components $G_{fy}$ and $\beta_{fy}$, respectively, as before noted for the corresponding measured values. However, these $G_{fy}$ and $\beta_{fy}$ depend on various mechanical properties. $G_{fy}$ and $\beta_{fy}$ are numerically computed for a large number of values of the mechanical properties. When the calculated $G_{fy}$ and $\beta_{fy}$ converge to the measured $G_{fy}$ and $\beta_{fy}$, the values used to calculate $G_{fy}$ and $\beta_{fy}$ are the correct values.

Many techniques may be used to determine when convergence occurs. For example, Newton-Raphson numerical iteration may be used to minimize residual functions that describe differences between experimentally measured values of $G_{fy}$ and $\beta_{fy}$ and their corresponding values calculated with eq. (7) based on trial values of mechanical properties. The analysis concludes when the values used for the mechanical properties give residual function values that meet specified convergence criteria. This method is described below in the determination of $l_F$, $\rho_F$, $\eta_F$, and $\mu_F$. Variables in eq. (7) which are not varied by computer must be chosen based on literature values or independent experimental determinations.

For example, the film thickness $l_F$ may be evaluated by the Behrndt method in which an amount of mass deposited onto an unloaded quartz resonator is assumed to be directly proportional to the change in the period of the resonator. This assumption is considered to be valid for elastic films for up to approximately 10% of the quartz mass.

The system described above can be used for measuring solvent dynamics in polymer films. Properties of thin films of polymers may be determined by the method of the invention. In the following example, a polystyrene film swollen in 2-chlorotoluene is studied while its chemical composition changes due to drying of the 2-chlorotoluene under ambient conditions.

A polystyrene/2-chlorotoluene film is prepared by spin coating one drop of 2-chlorotoluene containing 45% polystyrene on the metal electrode on one side of crystal 103. The molecular weight distribution of the polystyrene exhibits a bimodal distribution with 55% of the polymer having a number average molecular weight of 400 (a weight average molecular weight of 1200) and 45% of the polymer having a number average molecular weight of 40,000 (a weight average molecular weight of 150,000).

While this example uses spin coating, other methods of coating may also be used. These include spray coating, "doctor knife" or blade coating, roll coating, evaporative coating, plasma deposition, and various glass slide techniques.

After spin coating, the resonator lead wires, similar to leads 109 and 111 in FIG. 1, are wiped with a toluene-moistened swab to remove excess polymer solution that may prevent adequate electrical contact, and the resonator is connected to the impedance analyzer.

The resonant frequency and complex resonant admittance of the composite resonator may be measured every 80 seconds for the first three hours of drying and every 300 seconds thereafter. The film viscoelasticity is evaluated from the composite resonator measurement data.

Figure 4:
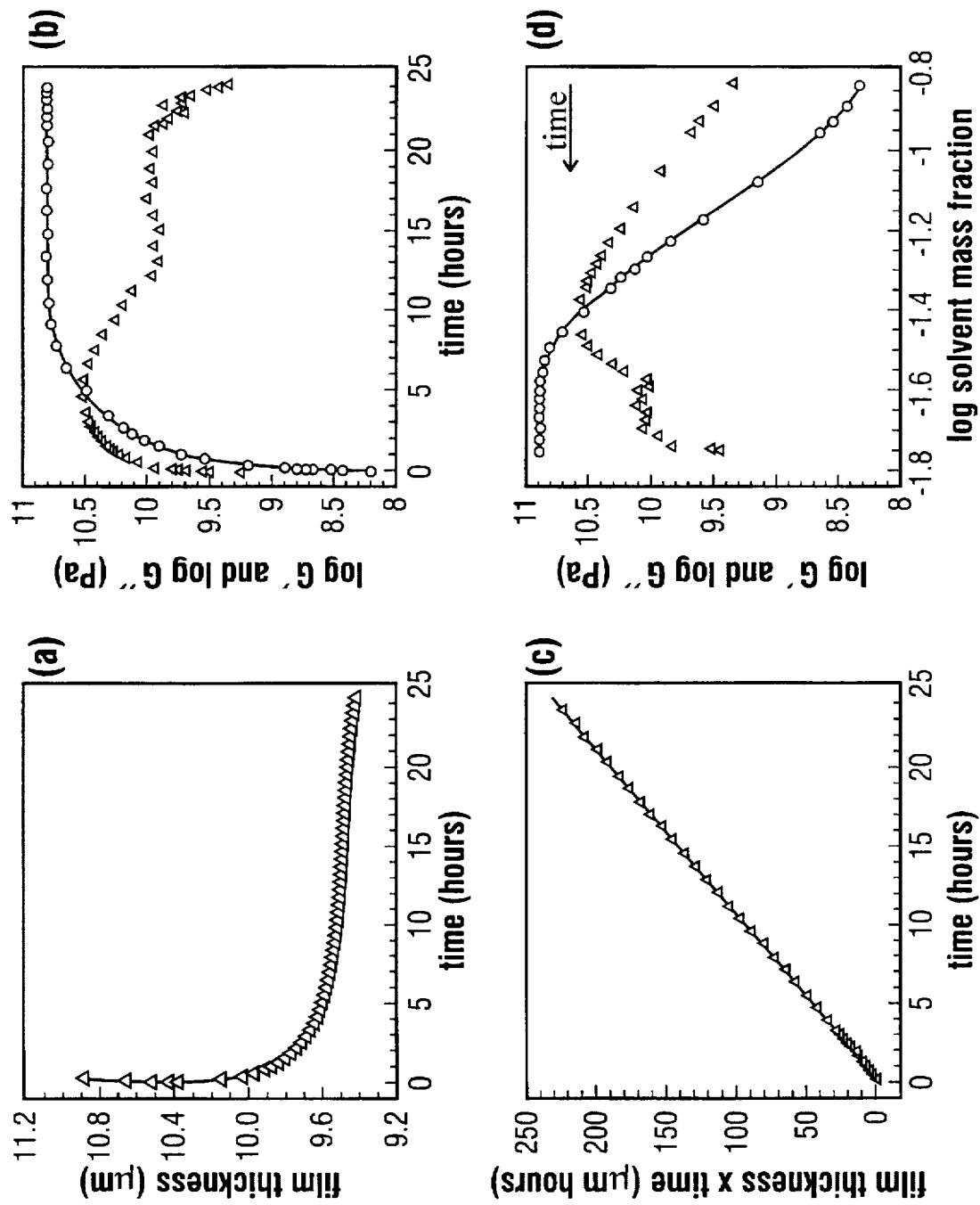
FIGS. 4(a)–(d) are graphs of (a) the thickness of a thin film versus time; (b) log G' and log G" of the thin film versus time, where these correspond to the logarithm of the storage and loss moduli, respectively; (c) the product of thickness and time versus time; and (d) log G' and log G" versus the log solvent mass fraction.

The solvent content decreases from 15.1% to 1.8% during drying. The film thickness as a function of time is shown in FIG. 4(a). The film's thickness decreases due to drying. One way of studying the film properties is to examine the mass fraction of solvent in the polymer film. To estimate the mass fraction of solvent in the polymer film, the film thickness versus time curve is linearized by using an empirical fit described by eq. (11) below, where $c_1$ and $c_2$ are constants that can be determined by linear regression of a plot of the combined variable $l_F t$ versus t (FIG. 4(c)).

$$l_F = \frac{c_1 + c_2 t}{t} \quad (11)$$

FIG. 4(b) depicts the values of G' (circles) and G" (triangles) calculated with the previously mentioned two-dimensional Newton-Raphson procedure from admittance data acquired at each time point during drying. A global maximum in G" is observed at ≈5 hours and is followed by a decrease until a plateau is reached at 12.3 hours. G" decreases once again after a total elapsed drying time of 21.6 hours. The final state of a small G" relative to G' is consistent with a fully dried glass. FIG. 4(d) exhibits the features observed in the data depicted in FIG. 4(b). The maximum in G" occurs at a solvent mass fraction of 3.7%, and the plateau region in G" corresponds to solvent mass fractions ranging from 2.7% to 2%.

Figure 5:
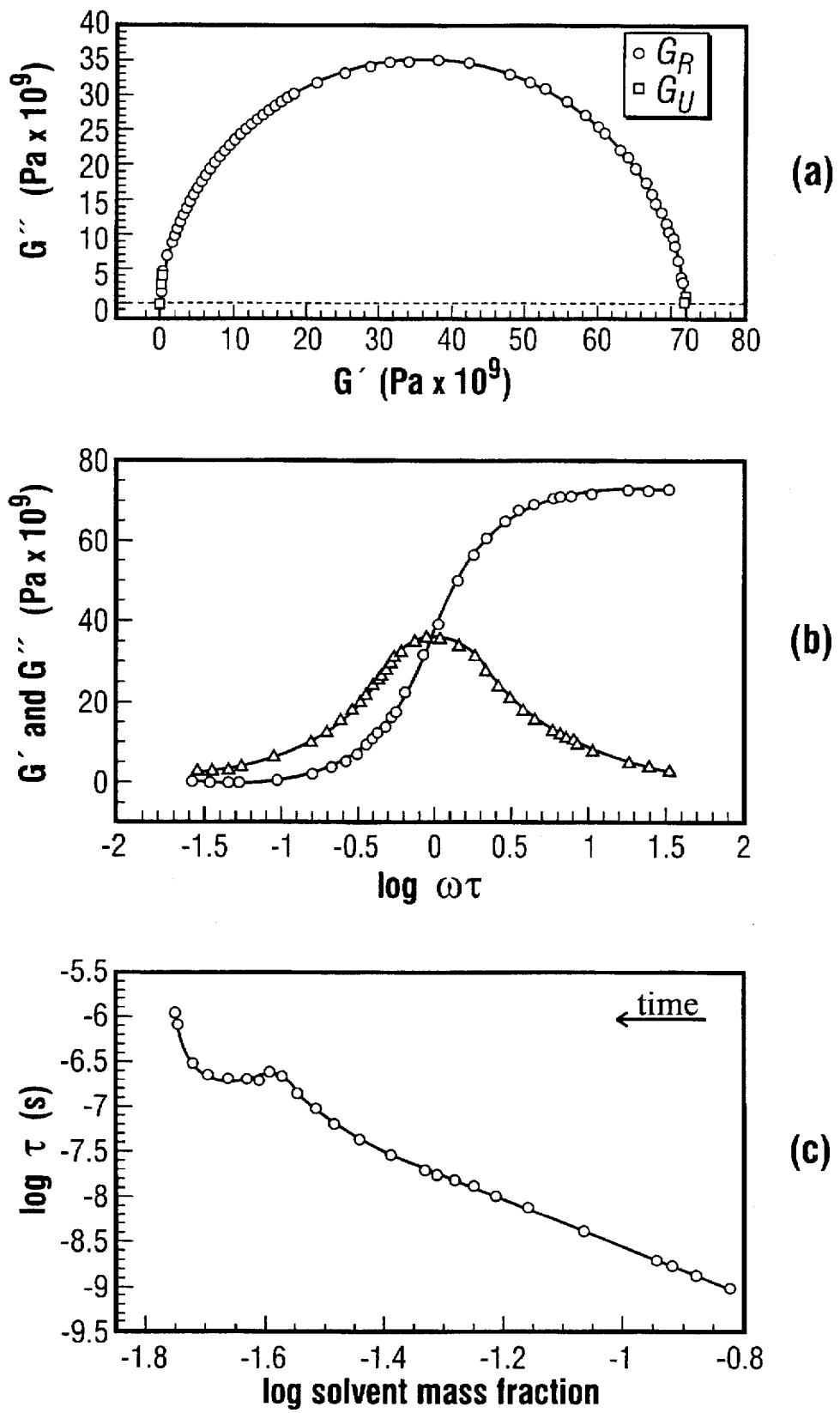
FIGS. 5(a)–(c) are graphs of (a) a Cole-Cole representation of G" versus G' of the thin film using data represented in FIG. 4(b) or 4(d); (b) G' and G" versus log $\omega^*\tau$ of the thin film; (c) log $\tau$ versus log solvent mass fraction of the thin film, where $\tau$ is the relaxation time of the thin film for a stress relaxation experiment (where strain is held constant).

FIG. 5(a) shows the trends in G' and G" described in terms of a Cole-Cole plot (a plot of G" versus G'). This data conforms to eqs. (12) and (13) below for a system defined by a single relaxation process, where $G_R$ is the relaxed modulus that represents the value of the storage modulus at such a low frequency (high solvent content) that all relaxations within the film move with the quartz resonator frequency, $G_U$ is the unrelaxed modulus that represents the value of the storage modulus at such a high frequency (low solvent content) that no relaxation occurs, and $\tau$ is the relaxation time for a stress relaxation experiment (strain is held constant).

$$G' = G_R + \frac{(G_U - G_R)\omega^2\tau^2}{1 + \omega^2\tau^2} \quad (12)$$

The data in FIG. 5(a) fit the behavior expected for a single relaxation process in which $G_R = 1.06 \times 10^8$ $$G'' = \frac{(G_U - G_R)\omega\tau}{1 + \omega^2\tau^2} \quad (13)$$

Pascals (Pa) and $G_U = 7.16 \times 10^{10}$ Pa. These values are obtained by an iterative procedure in which trial values of $G_R$ and $G_U$ and experimentally measured values of G' are used to solve exactly for $\omega\tau$ using eq. (12) at each solvent mass fraction investigated. The values of $\omega\tau$ obtained in this manner are then used to solve numerically for G" using eq. (13). The absolute difference between this fitted G" and the experimentally measured G", divided by the experimentally measured G", at each solvent mass fraction investigated represents the error of the single relaxation model fit at each data point. Iteration for the optimum $G_R$ and $G_U$ is continued by trial-and-error until the mean error representing all data points is minimized. The mean error in G" determined in this manner is 1.3%. In this case, the experimentally measured data are sufficiently complete that good estimates for $G_U$ and $G_R$ may be obtained directly by extrapolation to the x-axis of FIG. 5(a).

FIG. 5(b) shows plots of G' and G" versus the log of the combined dimensionless variable ωτ. These plots (solid lines) exhibit excellent agreement with the behavior expected for a single relaxation process, again described by eqs. (12) and (13), suggesting that the relaxation observed is indicative of solvent reorientational dynamics.

These results show that shear mode quartz resonators using the method of the invention can be used to investigate solvent dynamics in polymer films at high concentrations that are inaccessible by other experimental methods.

Figure 6:
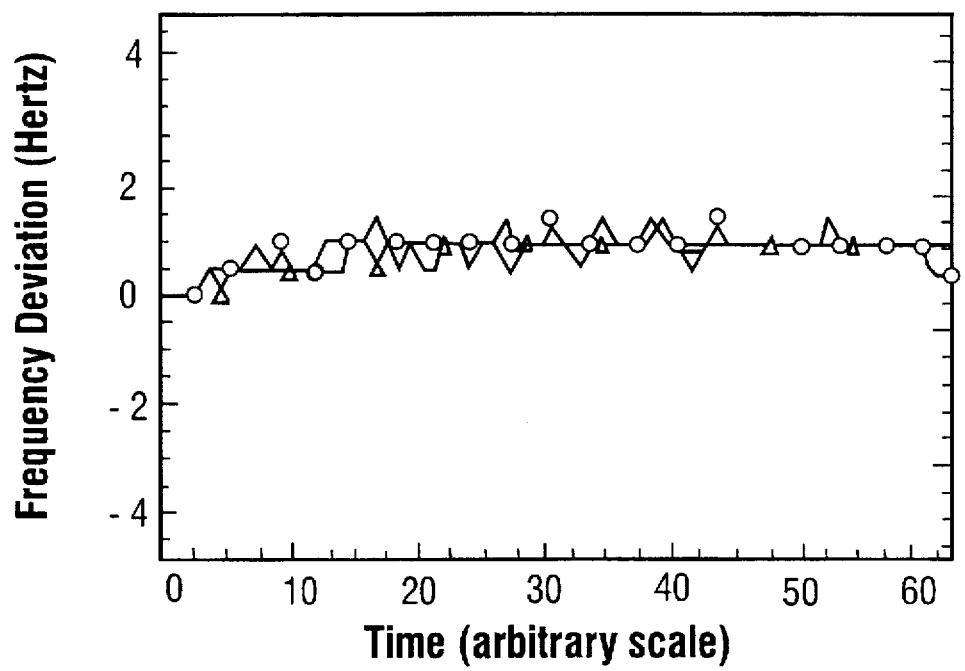
FIG. 6 is a graph of the deviation from initial value of the frequency of minimum absolute admittance for two quartz resonators.

The technique can also be used for determining the quality of quartz resonators. Embodiments of the invention may be used to determine the stability over time of two distinct AT-cut quartz resonators. In this example, both of the resonators have very stable resonant frequencies in time, as indicated by the time history of the resonant frequencies shown in FIG. 6. However, an embodiment of the invention shows that only one of these crystals has long-term stability in the real part of its resonant admittance.

Figure 7:
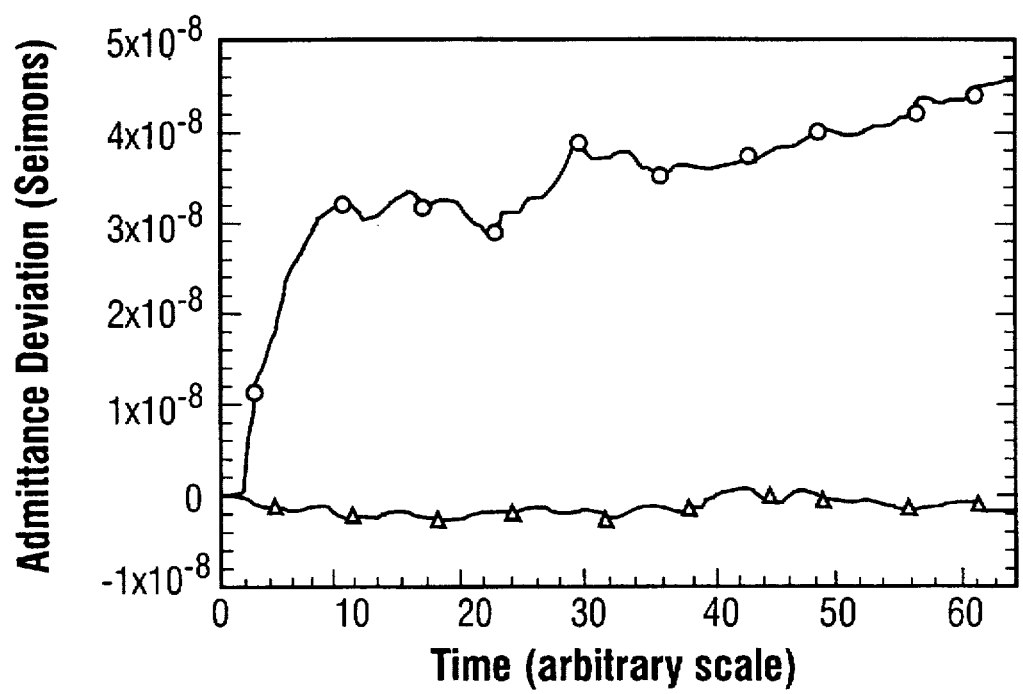
FIG. 7 is a graph of the deviation from initial value of the real component of the admittance at the frequency of minimum amplitude for the two quartz resonators of FIG. 6.

FIG. 7 shows the deviation of the real resonant admittance for the resonator represented by circles. The deviation is seen to be significant and increasing with time in comparison to the flat baseline for the resonator that is represented by triangles. This means that the resonator represented by triangles is far more stable than the resonator represented by circles. The method can therefore be implemented as part of a quality control process for distinguishing the stability of bare quartz resonators. An instability observed in the real resonant electrical admittance may be indicative of twinning or other mechanical defects in the quartz resonator.

Figure 8:
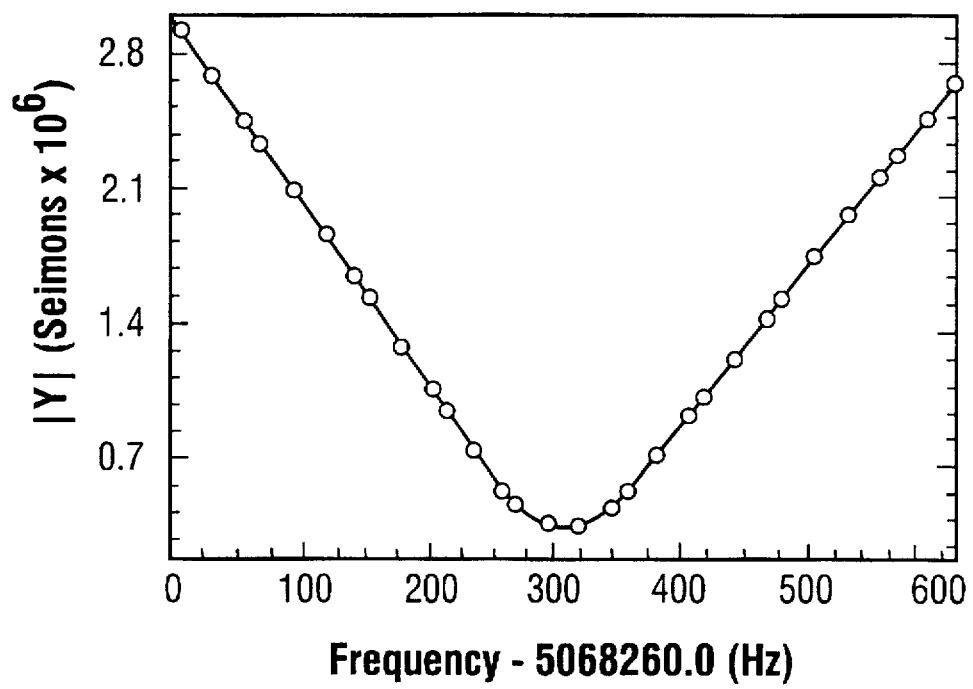
FIG. 8 is a graph of the absolute admittance versus frequency around the frequency of minimum absolute admittance for two quartz resonators represented by circles and lines, respectively.
Figure 9:
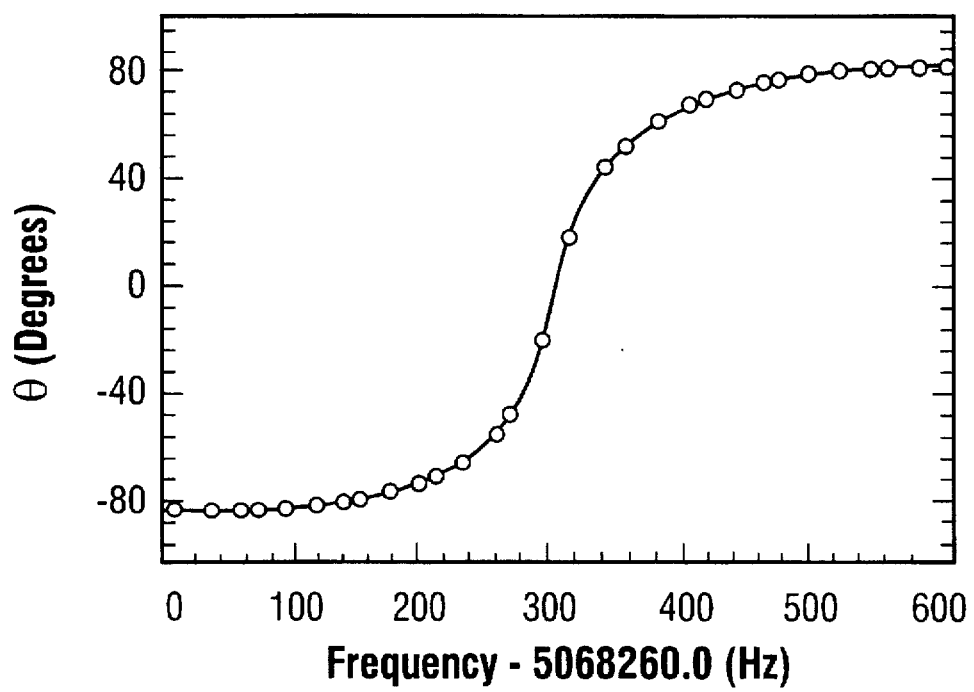
FIG. 9 is a graph of the phase angle versus frequency around the frequency of minimum absolute admittance for the two quartz resonators of FIG. 8.

A related application of the invention is to serve as a sensitive means for differentiating between quartz resonators. This application can be illustrated with the absolute admittance and phase angle data that are represented by FIGS. 8 and 9, respectively. These are obtained by performing impedance analysis on two distinct AT-cut quartz resonators in the vicinity of the frequency of minimum absolute admittance. A prior art method gives essentially the same resonant electrical characteristics for resonators I (the line) and II (the circles), since the difference in the plots for the two resonators is seen to be less than the resolution of most equivalent circuit curve-fitting routines, which sometimes have errors in excess of 50%.

The method of the invention may be applied to the data in the figures. The subtle difference in the resonant admittance plots between the two resonators, barely visible in FIGS. 8 and 9, creates a significant difference in their resonant electrical characteristics at $f_{Ymin}$. The resonant electric characteristics at $f_{Ymin}$ determined are shown in Table 1 for the two resonators.

The data in Table 1 show that resonator II has a positive resonant phase angle, and resonator I has a negative resonant phase angle. This negative resonant phase angle is due to defects in the electrical contacts of resonator I. As noted above, a quartz resonator by itself will not generally have a negative resonant phase angle because such a result is unphysical.

It is not generally possible to evaluate the resonant electric characteristics of resonator I even with an extremely accurate prior art curve fitting routine, since only positive values of the resonant phase

TABLE 1

Resonant Electric Characteristics for Resonators I and II

| Resonator | Resonant \|Y\| (Siemens) | Resonant Phase Angle θ | Resonant Frequency |
|---|---|---|---|
| I | $3.3041 \times 10^{-7}$ | −0.04400 Degrees | 5.06857268 MHz |
| II | $3.3301 \times 10^{-7}$ | 0.02809 Degrees | 5.06857408 MHz |

The technique may further be used for calibration of a quartz resonator. Usually an unloaded quartz resonator requires calibration prior to measurement. The calibration of an unloaded quartz resonator entails determining $f_Y$, $A_{ACT}$ and $\eta_q$. Once $f_Y$ is known $l_q$ can be determined using eq. (14) below, which can be derived by considering the thickness of a lossless quartz resonator. Although the finite thickness of the resonator electrodes can be taken into consideration, the electrodes may also be considered to have negligible thickness for most applications.

$$l_q = \frac{\sqrt{\dfrac{C_{66} + \dfrac{e_{26}^2}{\epsilon_{22}}}{\rho_q}}}{2 f_Y} \tag{14}$$

The calibration procedure first involves a measurement of $f_{Ymin}$, $G_{fYmin}$ and $\beta_{fYmin}$ with the transformation method described above. Setting $l_F=0$ for an unloaded quartz resonator gives the simplified form of eq. (7) below:

The quartz viscosity $\eta_q$ an energy dissipation factor of the unloaded quartz resonator. It can be uniquely determined from the dimensionless ratio of $$Y = -\frac{i\omega A_{ACT}\epsilon_{22} k_q C_{66}}{2\dfrac{e_{26}^2}{\epsilon_{22}}\tan\left(\dfrac{k_q l_q}{2}\right) - k_q l_q C_{66}} \tag{15}$$

$G_{fYmin}/\beta_{fYmin}$ referred to as the admittance ratio. The dependence of $\eta_q$ on the admittance ratio is given directly by eq. (15) since $A_{ACT}$ is cancelled when the real part of the equation is divided by the imaginary part. The Newton-Raphson method is used to find $\eta_q$ from eq. (15) given a particular resonant admittance ratio. A residual function F is defined that represents the difference between the experimentally measured admittance ratio and the admittance ratio based on eq. (15) given a particular value of $\eta_q$. This function can be expressed as eq. (16). Iteration, to give a value of $\eta_q$ that is consistent with the experimentally measured admittance ratio, is performed according to eq. (17) where $\eta_q^k$ represents the estimate of $\eta_q$ at the kth iteration, $\eta_q^{k+1}$ represents the estimate of $\eta_q$ at the k+1st iteration and $F^q(\eta_q^k)$ represents the derivative of the residual function with respect to $\eta_q$ and evaluated at $\eta_q^k$. Fourth order numerical differentiation is used to calculate $F^q(\eta_q^k)$ according to eq. (18) where h represents the step size. The convergence criteria used are $F(\eta_q)<5\times10^{-10}$ and $|\eta_q^{k+1}\eta_q^k|<5\times10^{-9}$ Pa-sec. Typical measured values of $\eta_q$ for unloaded quartz resonators used in this investigation range from 0.03 Pa-sec to 0.1 Pa-sec.

$$F(\eta_q^k) = \text{Experimentally Measured Admittance} \tag{16}$$
$$\text{Ratio} - \text{Admittance Ratio from eq. (15)}$$

$$\eta_q^{k+1} = \eta_q^k - \frac{F(\eta_q^k)}{F^q(\eta_q^k)} \tag{17}$$

-continued $$F^q(\eta_q^k) = \frac{F(\eta_q^k + 2h) + 8F(\eta_q^k + h) - 8F(\eta_q^k - h) + F(\eta_q^k - 2h)}{12h} \quad (18)$$

Once $\eta_q$ has been calculated in the manner described above, the only remaining unknown variable in the calibration of the unloaded quartz resonator is $A_{ACT}$. This variable is calculated by dividing the measured real or imaginary resonant admittance by the corresponding real or imaginary admittance per unit area given by eq. (15). Typical values of $A_{ACT}$ range from 0.160 cm² to 0.270 cm² for the quartz resonators employed in the current study. These values are often less than the geometric area of the crystal electrodes which is 0.277 cm². The reason for this difference is not entirely understood at this point, but it is hypothesized that crystal defects and twinning in the quartz crystal may decrease $A_{ACT}$ from its geometric value. The piezoelectric active area $A_{ACT}$ is assumed to be the same for the unloaded and composite resonators. This assumption is supported by studies on the effects of stressed materials, including polymer films, on the sensitivity of a quartz resonator. Although the distribution of sensitivity is often found to change upon film deposition, the integral sensitivity has been reported to remain nearly constant. This integral sensitivity is related to the piezoelectric active area since both represent the local piezoelectric sensitivity integrated across the cross-sectional area of the crystal. It is therefore expected that if the integral sensitivity does not change upon film deposition then the piezoelectric active area should also not change.

The calibration procedure described above is repeated (e.g., 200 repetitions) on an unloaded quartz resonator. This repetition is performed in order to average fluctuations and thereby obtain more accurate calibration parameters. Typical standard deviations in $A_{ACT}$ and $\eta_q$ are 0.8% of the parameter value.

The technique can also be used to determine $l_F$, $\rho_F$, $\eta_F$, and $\mu_F$. Once an unloaded quartz resonator has been calibrated in the manner described above, it may be coated with the film of interest. Impedance analysis may be used to measure $f_{Y_{min}}$, $G_{Y_{min}}$, and $\beta_{Y_{min}}$ of the composite resonator. These measured variables are then used to determine the only remaining unknowns in eq. (7) namely, $l_F$, $\rho_F$, $\eta_F$, and $\mu_F$. The variables $l_F$ and $\rho_F$ are evaluated as discussed above.

The two-dimensional Newton-Raphson method with fourth order numerical differentiation is employed to evaluate $\eta_F$ and $\mu_F$. The residual functions used in the Newton-Raphson scheme are given by eqs. (19) and (20), where R represents the residual function for the real part of eq. (7) and C represents the residual function for the imaginary part of eq. (7).

$R(\eta_F^k, \mu_F^k)$=Experimentally Measured $G_{F_{Y_{min}}}$−G[eq. (7)] at $(\eta_F^k, \mu_F^k)$ $C(\eta_F^k, \mu_F^k)$=Experimentally Measured $\beta_{F_{Y_{min}}}$−β[eq. (7)] at $(\eta_F^k, \mu_F^k)$ The above residual functions are used to evaluate new guesses for $\eta_F$ and $\mu_F$ by an iterative procedure given by eqs. (21) and (22) where $\eta_F^k$ represents the estimate of $\eta_F$ at the kth iteration, $\eta_F^k$ represents the estimate of $\eta_F$ at the k+1st iteration, $\mu_F^{k+1}$ represents the estimate of $\mu_F$ at the kth iteration and $\mu_F^{k+1}$ represents the estimate of $\mu_F$ at the k+1st iteration. The equations for finding the required first derivatives by fourth order numerical differentiation are similar in form to eq. (18). For $R(\eta_F, \mu_F)$, they are given by eqs. (23) and (24) where h represents the step size. The equations for numerically differentiating $C(\eta_F, \mu_F)$ are identical in form. Successive implementation of eqs. (21) and (22) yields $\eta_F$ and $\mu_F$ that satisfy eq. (17) with the measured resonant frequency and complex admittance. Convergence to the correct $\eta_F$ and $\mu_F$ is defined by the criteria in eqs. (25) and (26).

$$\eta_F^{k+1} = \eta_F^k - \frac{R(\eta_F^k, \mu_F^k)\frac{\partial C(\eta_F^k, \mu_F^k)}{\partial \mu_F^k} - C(\eta_F^k, \mu_F^k)\frac{\partial R(\eta_F^k, \mu_F^k)}{\partial \mu_F^k}}{\frac{\partial R(\eta_F^k, \mu_F^k)}{\partial \eta_F^k}\frac{\partial C(\eta_F^k, \mu_F^k)}{\partial \mu_F^k} - \frac{\partial R(\eta_F^k, \mu_F^k)}{\partial \mu_F^k}\frac{\partial C(\eta_F^k, \mu_F^k)}{\partial \eta_F^k}} \quad (21)$$

$$\frac{\partial R(\eta_F^k, \mu_F^k)}{\partial \eta_F^k} = \frac{R(\eta_F^k + 2h, \mu_F^k) + 8R(\eta_F^k + h, \mu_F^k) - 8R(\eta_F^k - h, \mu_F^k) + R(\eta_F^k - 2h, \mu_F^k)}{12h}$$

$$\mu_F^{k+1} = \mu_F^k - \frac{R(\eta_F^k, \mu_F^k)\frac{\partial C(\eta_F^k, \mu_F^k)}{\partial \eta_F^k} - C(\eta_F^k, \mu_F^k)\frac{\partial R(\eta_F^k, \mu_F^k)}{\partial \eta_F^k}}{\frac{\partial R(\eta_F^k, \mu_F^k)}{\partial \eta_F^k}\frac{\partial C(\eta_F^k, \mu_F^k)}{\partial \mu_F^k} - \frac{\partial R(\eta_F^k, \mu_F^k)}{\partial \mu_F^k}\frac{\partial C(\eta_F^k, \mu_F^k)}{\partial \eta_F^k}} \quad (22)$$

$$\frac{\partial R(\eta_F^k, \mu_F^k)}{\partial \mu_F^k} = \frac{R(\eta_F^k, \mu_F^k + 2h) + 8R(\eta_F^k, \mu_F^k + h) - 8R(\eta_F^k, \mu_F^k - h) + R(\eta_F^k, \mu_F^k - 2h)}{12h}$$

$$\sqrt{R(\eta_F^k, \mu_F^k)^2 + C(\eta_F^k, \mu_F^k)^2} < 1 \times 10^{-10} \text{ Siemons} \quad (25)$$

$$\sqrt{\left(\frac{\eta_F^{k+1} - \eta_F^k}{\eta_F^k}\right)^2 + \left(\frac{\mu_F^{k+1} - \mu_F^k}{\mu_F^k}\right)^2} < 1 \times 10^{-10} \quad (26)$$

The present invention has been described in terms of a preferred embodiment. The invention, however, is not limited to the embodiment depicted and described. Rather, the scope of the invention is defined by the appended claims.

What is claimed is:

1. A method of determining mechanical properties of a system of a material mechanically coupled to an oscillating crystal, comprising:

(a) measuring measured components of a complex admittance of the system at an antiresonant frequency;

(b) calculating a range of values of theoretical components of the complex admittance by substituting a range of values of at least one mechanical property into an expression for the theoretical components of the complex admittance; and (c) determining when the theoretical components of the complex admittance are within a predetermined deviation from the measured components of the complex admittance.

2. The method of claim 1, wherein step (a) includes:

(d) measuring the magnitude and phase angle of the complex admittance as a function of frequency; and (e) transforming the magnitude and phase angle to transformed variables, such that the transformed variables of magnitude and phase angle are substantially linear functions of frequency.

3. The method of claim 1, wherein the crystal is a quartz crystal oscillator.

4. The method of claim 1, wherein the material is a polymer film coated on the crystal.

5. The method of claim 4, wherein the material property measured is related to material viscoelasticity.

6. The method of claim 4, wherein the material property measured is a storage modulus.

7. The method of claim 4, wherein the material property measured is a loss modulus.

8. The method of claim 4, wherein the material property measured is related to stress.

9. A method of determining mechanical properties of a piezoelectric crystal, comprising:

(a) measuring at least one component of the complex admittance of the crystal at an antiresonance frequency;

(b) calculating a range of values of the at least one component of the complex admittance by substituting a range of values of at least one mechanical property into an expression for the at least one component of the complex admittance;

(c) determining when the calculated values of the at least one component of the complex admittance is within a predetermined deviation from the measured values of the at least one component of the complex admittance.

10. The method of claim 9, wherein the piezoelectric crystal is a quartz crystal.

11. The method of claim 9, wherein the at least one component of the complex admittance is the real part of the complex admittance.

12. A method of calibrating a piezoelectric crystal oscillator, comprising the steps of:

(a) measuring measured components of the complex admittance of the system at an antiresonance frequency, the measured components including the measured conductance and the measured susceptance;

(b) calculating a measured admittance ratio by dividing the measured conductance by the measured susceptance;

(c) calculating a range of values of theoretical admittance ratios by substituting a range of values of at least one mechanical property into an expression for the theoretical admittance ratio;

(d) determining when the theoretical admittance ratio is within a predetermined deviation from the measured admittance ratio; and (e) outputting the value of the mechanical property when the theoretical admittance ratio is within a predetermined deviation from the measured admittance ratio.

13. The method of claim 12, wherein the mechanical property is the crystal viscosity.

14. The method of claim 12, wherein the crystal is a quartz crystal.

15. A method of measuring the complex admittance and frequency in an antiresonance condition for a composite resonator, comprising the steps of:

(a) finding the approximate anti-resonant condition frequency region by direct measurement;

(b) transforming real and imaginary components of electric characteristics, or functions thereof, in the frequency range determined in step (a), into transformed variables that are substantially linear with frequency; and (c) determining antiresonant complex admittance and frequency from curve fits of the transformed variables.

16. A method of measuring the complex admittance and frequency in an antiresonance condition for an unloaded piezoelectric crystal resonator, comprising the steps of:

(a) finding the approximate anti-resonant condition frequency region by direct measurement;

(b) transforming real and imaginary components of electric characteristics, or functions thereof, in the frequency range determined in step (a), into transformed variables that are substantially linear with frequency; and (c) determining antiresonant complex admittance and frequency from curve fits of the transformed variables.

* * * * *